United States Patent [19]
Wand et al.

[11] Patent Number: 5,180,520
[45] Date of Patent: Jan. 19, 1993

[54] FERROELECTRIC LIQUID CRYSTAL COMPOSITIONS CONTAINING HALOGENATED CORES AND CHIRAL HALOGENATED CORES AND CHIRAL HALOALKOXY TAIL UNITS

[75] Inventors: Michael Wand; Rohini Vohra; David Walba, all of Boulder, Colo.

[73] Assignee: University Research Corporation, Boulder, Colo.

[21] Appl. No.: 556,161

[22] Filed: Jul. 20, 1990

Related U.S. Application Data

[63] Continuation-in-part of Ser. No. 164,233, Mar. 4, 1988, Pat. No. 5,051,506.

[51] Int. Cl.$^5$ .................. C09K 17/34; C07D 239/02; C07D 213/24
[52] U.S. Cl. .................. 252/299.61; 252/299.01; 544/245; 544/335; 546/339; 546/346
[58] Field of Search .............. 252/299.01, 299.61, 252/299.62, 299.63, 299.64, 299.65, 299.66, 299.67; 564/298, 245, 335; 546/339, 346

[56] References Cited

U.S. PATENT DOCUMENTS

| | | | |
|---|---|---|---|
| 4,556,727 | 12/1985 | Walba et al. | 560/73 |
| 4,695,650 | 9/1987 | Walba et al. | 560/109 |
| 4,725,688 | 2/1988 | Taguchi et al. | 544/298 |
| 4,728,458 | 3/1988 | Higuchi et al. | 252/299.65 |
| 4,777,280 | 10/1988 | Eidman et al. | 558/389 |
| 4,781,857 | 1/1988 | Inoue et al. | 252/299.61 |
| 4,795,587 | 1/1989 | Ohno et al. | 252/299.61 |
| 4,798,680 | 1/1989 | Nohira et al. | 252/299.01 |

FOREIGN PATENT DOCUMENTS

| | | |
|---|---|---|
| 0220747 | 5/1987 | European Pat. Off. |
| 0225236 | 2/1988 | European Pat. Off. |
| 0263437 | 4/1988 | European Pat. Off. |
| 0267585 | 5/1988 | European Pat. Off. |
| 0269062 | 6/1988 | European Pat. Off. |
| 0278665 | 8/1988 | European Pat. Off. |
| 62-111939 | 5/1987 | Japan |
| 62-258361 | 11/1987 | Japan |
| 63-264573 | 11/1988 | Japan |
| 8606373 | 11/1986 | PCT Int'l Appl. |
| 8705018 | 8/1987 | PCT Int'l Appl. |
| 8902425 | 3/1989 | PCT Int'l Appl. |

OTHER PUBLICATIONS

Wand et al. (1991) Ferroelectrics 121:219-223.
Furukawa et al. (1988) Ferroelectrics 85:451-459.
Chemical Abstract No. 109:201686w (p. 795).

*Primary Examiner*—Robert L. Stoll
*Assistant Examiner*—Shean C. Wu
*Attorney, Agent, or Firm*—Greenlee & Winner

[57] ABSTRACT

The subject application discloses chiral nonracemic compositions of the general formula:

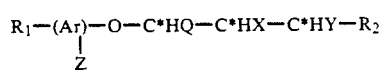

wherein $R_1$ is an achiral tail of two to sixteen carbons; Ar is an achiral FLC core of at least two rings; * denotes a chiral or potentially chiral carbon; Q is H or a methyl group; X and Z are halides and Y is H or a halide; and $R_2$ is one to ten carbon atoms. The —O—C*HQ—C*HX—C*HY— segment comprises the chiral proximal segment of the chiral tail. Z can be an ortho halide alone, or ortho and meta halides on adjacent carbons on the aromatic ring of the core adjacent to the proximal segment. $R_2$ is the distal segment of the chiral tail. The proximal segment is selected from the diastereomers and enantiomers:

| | |
|---|---|
| 2S-halo | 2R-halo |
| 1S-methyl-2S-halo | 1R-methyl-2R-halo |
| 1S-methyl-2R-halo | 1R-methyl-2S-halo |
| 2S,3S-dihalo | 2R,3R-dihalo |
| 2R,3S-dihalo | 2S,3R-dihalo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2R,3S-dihalo | 1S-methyl-2S,3R-dihalo |
| 1R-methyl-2R,3S-dihalo | 1S-methyl-2S,3R-dihalo |

10 Claims, No Drawings

FERROELECTRIC LIQUID CRYSTAL COMPOSITIONS CONTAINING HALOGENATED CORES AND CHIRAL HALOGENATED CORES AND CHIRAL HALOALKOXY TAIL UNITS

This invention was made with partial support States Government under National Science Foundation Grant no. ISI8860992. The United States Government has certain rights in this invention.

RELATEDNESS OF THE APPLICATION

This application is a continuation-in-part of U.S. Ser. No. 164,233, filed Mar. 4, 1988 now U.S. Pat. No. 5,051,506 which is incorporated herein in its entirety by reference.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwall in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications. A recent review of the applications of FLC devices is given by Lagerwall, S. T. and Clarke, N. A. (1989) Ferroelectrics 94:3–62.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$.

There are a number of reports of compounds containing phenylbenzoate, biphenyl, phenylpyrimidine and related cores coupled to chiral tail units which possess monotropic smectic C* phases displaying fast switching speeds at room temperature, or which can be employed as FLC dopants to induce high polarization and fast switching speeds when combined in mixtures with FLC host materials.

The following are exemplary reports of such FLC compounds:

Walba et al., U.S. Pat. No. 4,556,727 reports phenylbenzoates having non-racemic 2-alkoxy-1-propoxy tails.

Eidman and Walba, U.S. Pat. No. 4,777,280 report chiral 1-cyanoalkoxy phenylbenzoates. Walba and Razavi, U.S. Pat. No. 4,695,650 report chirally asymmetric reverse ester phenylbenzoates having chiral 1-haloalkyl tail units.

Ohno et al. (1989) U.S. Pat. No. 4,795,587 refers to liquid crystal compounds exhibiting smectic C phases which contain a phenylpyridine core having the formula:

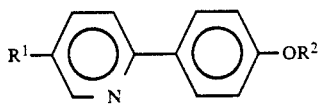

where $R^1$ is an alkyl group having seven to twelve carbon atoms and $R^2$ is an alkyl group having five to twelve carbon atoms.

Japanese patent documents JP 63264573 and JP 62258361 refer to optically active 6-substituted-pyridine-3-carboxylic acid esters useful as ferroelectric smectic liquid crystals. Optically active 6-substituted-pyridine-3-carboxylic acid esters obtained from reaction of dodecyloxybenzoic acid, thionyl chloride and 6-hydroxynicotinic acid (S)-2-methylbutyl ester are specifically referred to. Japanese patent document JP 62175465 refers to ester compounds contained in liquid crystal compositions exhibiting nematic phases. 2-(trans-4-ethyl-cyclohexyl)- 5-nicotinic acid-3-fluoro-4-cyanophenyl ester is referred to specifically.

Walba et al. (1986) J. Amer. Chem. Soc. 108:7424-7425 and Walba and Vohra, U.S. Pat. No. 4,648,073 and U.S. Pat. No. 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

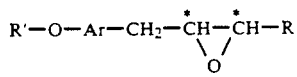

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

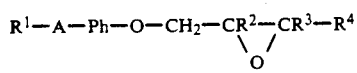

where A is a diazine-2,5,-diyl or diazine-3,6-diyl, $R^1$ is a straight chain or branched alkyl group having 1-12 carbon atoms wherein one or two non-neighboring $CH_2$ groups is replaced with an O or S atom, $R^{2-4}$ are, independent of one another, H, a straight chain alkyl group having 1-12 carbon atoms or a branched alkyl group having 3-10 carbon atoms wherein $R^1$, $R^2$ and $R^3$ are not all H. Compounds in which $R^2$ and $R^3$ are both H having extrapolated polarization densities ($P_{ext}$) in the range from 30-70 nC/cm$_2$ are reported.

Walba and Razavi, U.S. Pat. No. 4,835,295, discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

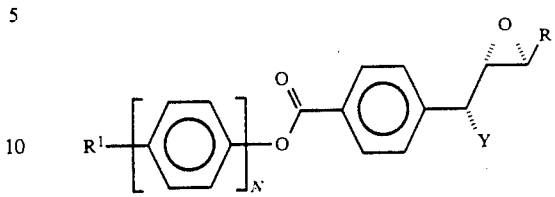

where R' is alkyl alkoxyl having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the relative alignment of the epoxide and halogen bond dipoles in the isomer.

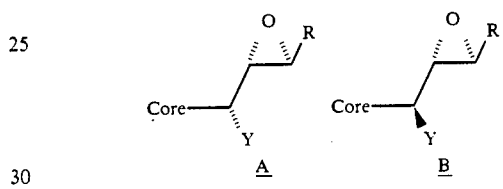

Furukawa K. et al. (1988) Ferroelectrics 85:451-459 refers to chiral smectic C compounds having an ester group in the core and an optically active tail group, either alkoxy or alkoxy carbonyl, with an electronegative substituent, either a halogen or cyano group, ortho to the chiral tail, for example:

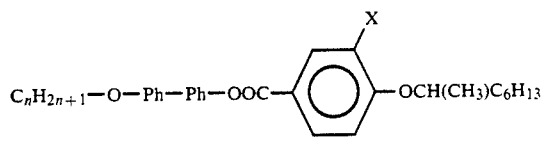

where X=H, Halogen or CN.

While a number of useful ferroelectric liquid crystal materials (both pure compounds and mixtures) have been reported, there is a growing need for FLC materials with varying properties of temperature range, tilt angle and switching speed for use in varied applications. Further, there is a need for FLC dopants with varying mixing properties (which are dependent, at least in part, on chemical composition) for use in the preparation of FLC mixtures. FLC dopants which impart high polarization density to, and retain low viscosity in, such mixtures are of particular interest.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The composition of the subject invention comprises chiral nonracemic compositions of the general formula:

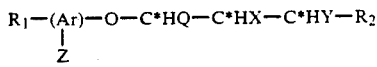

wherein:

$R_1$ is an achiral tail of two to sixteen carbons; Ar is an achiral FLC core of at least two rings; * denotes a chiral or potentially chiral carbon; Q is H or a methyl group; X and Z are halides and Y is H or a halide; and $R_2$ is one to ten carbon atoms. $R_2$ is the distal segment of the chiral tail. The —O—C*HQ—C*HX—C*HY— segment comprises the chiral proximal segment of the chiral tail; the proximal segment is selected from the diastereomers and enantiomers:

| | |
|---|---|
| 2S-halo | 2R-halo |
| 1S-methyl-2S-halo | 1R-methyl-2R-halo |
| 1S-methyl-2R-halo | 1R-methyl-2S-halo |
| 2S,3S-dihalo | 2R,3R-dihalo |
| 2R,3S-dihalo | 2S,3R-dihalo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2R,3S-dihalo | 1S-methyl-2S,3R-dihalo |
| 1R-methyl-2R,3S-dihalo | 1S-methyl-2S,3R-dihalo. |

The preferred proximal segments are:

| | |
|---|---|
| 2S-halo | 2R-halo |
| 1S-methyl-2S-halo | 1R-methyl-2R-halo |
| 2S,3S-dihalo | 2R,3R-dihalo |
| 1S-methyl-2R,3R-dihalo | 1R-methyl-2S,3S-dihalo. |

The achiral cores are rigid, linear moieties. Preferred cores are those that are chemically stable and which do not impart high orientational viscosity in the liquid crystal phase. In the present invention, cores containing at least two aromatic rings are preferred such as those cores based on phenylbenzoate, biphenylbenzoate, phenylpyrimidine, biphenylpyrimidine, phenylpyridine, biphenylpyridine or biphenyl structures. As used herein "phenylbenzoate" includes forward and reverse phenylbenzoates:

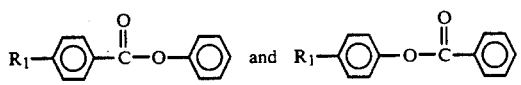

"Phenylpyrimidine" means 2,5-substituted phenylpyrimidines. Additionally, "phenylpyridine" means 2,5-substituted phenylpridines.

Each of the cores of the present invention are halogenated in the aromatic ring adjacent to the chiral tail. Halogenation is either at a single ortho position or at one ortho and one meta position on adjacent carbons on the same side of the ring. When referring to the location of the halide(s), "ortho" and "meta" mean relative to the chiral tail. For example, the positions of halides on the aromatic ring adjacent to the chiral tail can be as follows:

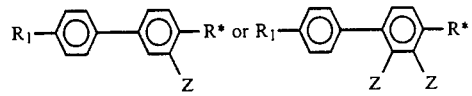

$R_1$ is the achiral tail and $R^*$ indicates the chiral tail, including the proximal and distal ($R_2$) segments. The chiral tail is positioned at the para position on its aromatic ring relative to the bond of its ring to the adjacent ring or to carbon or oxygen atoms bridging its ring to the adjacent ring. Likewise, the achiral tail is positioned at the para position on its aromatic ring relative to the bond of its ring to the adjacent ring or to carbon or oxygen atoms bridging its ring to the adjacent ring. For example, in a biphenyl core, the chiral and achiral tails are positioned 4,4'.

If there is both a meta and ortho halide on the core, they can be the same or different halides. The symbol Z can mean an ortho halide alone, or ortho and meta halides on adjacent carbons; in the latter case, the halide in the ortho position can be different than that in the meta position.

Table 1 illustrates some of the preferred and less preferred ferroelectric (FLC) cores useful in synthesizing the compounds of the subject invention. Cores comprising a pyridine or pyrimidine ring are preferably designed with the nitrogens in rings non-adjacent to the chiral tail. Again, Z indicates a halide or halides located on the ring either in one ortho position alone or at one ortho and one meta position on adjacent carbons.

The achiral tail, $R_1$, can be an alkyl, alkenyl or alkoxy group. $R_1$ can contain two to sixteen carbon atoms; it preferably contains five to sixteen carbons; and it most preferably contains eight carbons. $R_1$ can be straight chain or branched. Branching can broaden the smectic C* phase of the compound itself or of an FLC mixture containing the compound. The branching effect is enhanced when branching is more distant from the core. It has also been observed that if branching occurs at carbons 2-8 (relative to the core), the polarization density of the FLC molecule is generally not significantly affected.

As described in PCT/EP88/00724 (WO 02425, p.13), oxygen or sulfur atoms can replace non-adjacent $CH_2$ groups in the achiral tail to produce, for example, alkoxy or thiaalkyl tails. It has been observed that such substitutions do not significantly impair the polarization density; such substitutions can impart a broader smectic C* phase of the compound itself or in an FLC mixture containing the compound.

When $R_1$ is an alkenyl, the double bonds can be located at any position in $R_1$'s chain, including the omega position. Positioning of a double bond in the omega position creates a precurser to an FLC polymer. For example, an FLC compound of the subject invention containing omega-alkenyl achiral tails could be reacted with polysiloxane to form a polymeric FLC.

TABLE 1
| Preferred Cores | Less Preferred Cores |
|---|---|
| 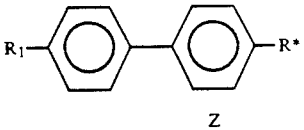 | 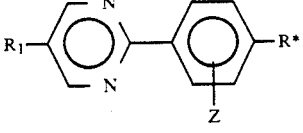 |
| 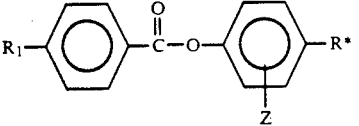 | 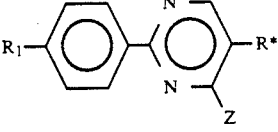 |
| 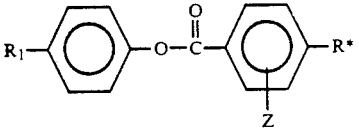 | 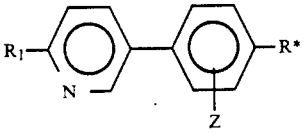 |
| 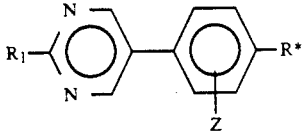 | 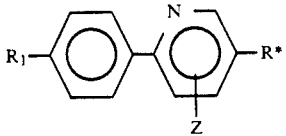 |
| 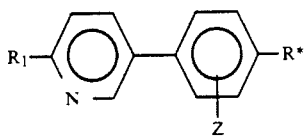 | 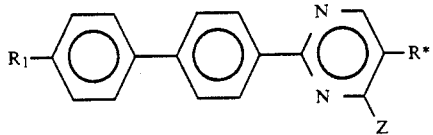 |
| 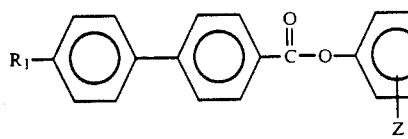 | 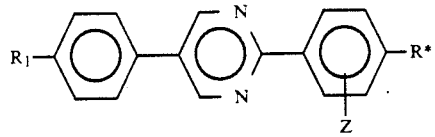 |
| 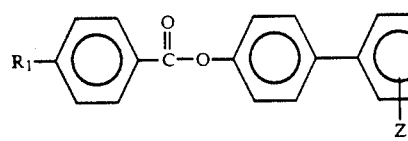 | 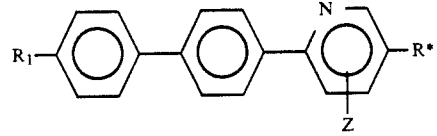 |
| 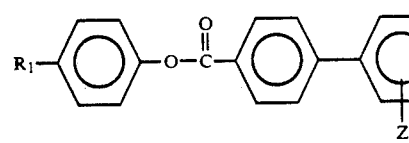 | 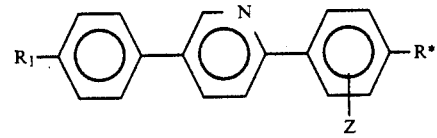 |
| 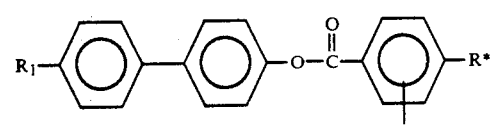 | |
|  | |

TABLE 1-continued

| Preferred Cores | Less Preferred Cores |
|---|---|
| ![core structure with pyridazine, phenyl, phenyl; R₁ on pyridazine, R* on phenyl with Z substituent] | |
| ![core structure with phenyl, pyrimidine, phenyl; R₁, R*, Z] | |
| ![core structure with phenyl(N), phenyl, phenyl; R₁, R*, Z] | |
| ![core structure with phenyl(N), phenyl, phenyl; R₁, R*, Z] | |
| ![core structure with phenyl, phenyl(N), phenyl; R₁, R*, Z] | |

When $R_1$ is an alkenyl, the double bonds can be cis or trans. However, trans bonds are preferred because cis is likely to result in reduced solubility of the dopant FLC in the host material. Additionally, cis bonds can narrow the smectic C* range of the compound itself or of an FLC mixture containing the compound.

The halides of the chiral proximal segment are preferably fluorine and chlorine. X, Y and Z can be the same or different halides.

It has been observed that FLC dopants comprising one enantiomer of an enantiomer pair, such as:

| Enantiomer Pairs | | |
|---|---|---|
| 2S-halo | and | 2R-halo |
| 1S-methyl-2S-halo | and | 1R-methyl-2R-halo |
| 1S-methyl-2R-halo | and | 1R-methyl-3S-halo |
| 2S,3S-dihalo | and | 2R,3R-dihalo |
| 2R-3S-dihalo | and | 2S,3R-dihalo |
| 1R-methyl-2R,3R-dihalo | and | 1S-methyl-2S,3S,dihalo |
| 1R-methyl-2R,3S-dihalo | and | 1S-methyl-2S,3R-dihalo |
| 1R-methyl-2S,3S-dihalo | and | 1S-methyl-2R,3R-dihalo |
| 1R-methyl-2S,3R-dihalo | and | 1S-methyl-2R,3S-dihalo | function equivalently in FLC host materials as the FLC dopant comprising the other enantiomer of the enantiomer pair, except that the sign of their polarization densities is reversed. As will be understood by those in the art, the sign of the polarization of an FLC dopant should be the same as that of the host material in order to achieve high polarization mixtures. It is a feature of this invention that either enantiomer of the above-identified enantiomer pairs can be prepared. This allows choice of the appropriate enantiomers for use with a particular host material.

The distal segment ($R_2$) of the chiral tail of the composition of the subject invention can be an alkyl or alkenyl group of one to ten carbons. As the size of the distal segment increases, it can increase the viscosity of the FLC compound; for this reason, it is preferred that $R_2$ contain two to three carbons.

$R_2$ can be straight chain or branched. Branching can broaden the smectic C* phase; generally, this effect is enhanced when branching is more distant from the core.

If $R_2$ is an alkenyl, the double bonds can be located at any position in the segment. If $R_2$ contains double bonds, they may be cis or trans. However, trans bonds are preferred because cis bonds are likely to result in reduced solubility of the dopant FLC in the host material. Additionally, cis bonds are likely to narrow the smectic C* range of the compound itself or of an FLC mixture containing the compound.

$R_2$ can contain chiral carbons. Chirality in the distal segment, like that in the proximal segment, contributes to polarization density of the FLC molecule. The distal segment chirality can enhance or reduce the polarization density of the FLC molecule as imparted by the proximal segment. The closer the chiral groups in the distal segment to the proximal segment, the greater the impact of the $R_2$ chirality on the dipole created by the proximal segment. Whether a particular chiral $R_2$ enhances or decreases polarization density can be determined by routine testing by known methods of FLC compounds containing the chiral $R_2$ in question. Synthesis methods of $R_2$-containing FLC compounds of the subject invention are described hereinbelow and/or are known to those of skill in the art. Methods for measuring polarization density are also described hereinbelow.

DETAILED DESCRIPTION OF THE INVENTION

The compositions of the subject invention are synthesized by several methods, described hereinbelow, from a 4',4-substituted

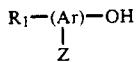

compound, wherein Z represents either an orthohalide or meta and ortho halides on adjacent carbons on Ar. The 4',4-substituted

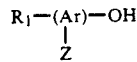

compounds are either commercially available or can be synthesized by known methods from readily available starting materials. For example, the synthesis of 4'-decyloxyphenyl-3-fluoro-4-hydroxybenzoate (X, where $R_1$=decyloxy and Z=F) is described in the Examples.

In the Examples, the Ar employed is phenylbenzoate; however, as discussed hereinabove, any suitable FLC core can be used in place of phenylbenzoate.

To synthesize a chiral 4'-$R_1$-phenyl-4-[(2,3-dihalo)alkoxy]-3-halobenzoate, a chiral 2,3-epoxy alkanol is coupled to the 4',4-substituted

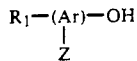

compound; the epoxy ring is opened and treated with halogenating agents. Scheme 3 illustrates the synthesis of a 4'-$R_1$-phenyl-4-(2R,3R-dihalo)alkoxy-3-halobenzoate (XIV). As an example, the synthesis of 4'-decyloxyphenyl-4-[(2R,3R-difluoro)hexyloxy]-3-fluorobenzoate (XIV, where $R_1$=decyloxy, X, Y and Z=F, and $R_2$=propyl) follows Scheme 3 and is discussed in Example 3a.

To synthesize the enantiomer of the 4'-$R_1$-phenyl-4-[(2R,3R -dihalo)alkoxy]-3-halobenzoate (XIV) produced by the method Example 2a, the method of Example 2a is followed with the exception that the (2S,3S-epoxy)hexanol (XI, where $R_2$=propyl) is replaced with its enantiomer, (2R,3R-epoxy)hexanol.

The syntheses of the diastereomers of the 4'-$R_1$-phenyl-4-(2R,3R-dihalo)alkoxy-3-halobenzoate (XIV) produced by the method of Example 2a, can be accomplished by methods known to those of skill in the art from readily available materials, or as illustrated in the Examples below, i.e, the synthesis of 4'-decyloxyphenyl-4-[(2R,3S-difluoro)hexyloxy]-3-fluorobenzoate.

To synthesize 4'-$R_1$-phenyl-4-[(2S-halo)alkoxy]-3-halobenzoates (XVI), the method of Example 3a is followed. This method involves the coupling of 4'-$R_1$-phenyl-3-halo-4-hydroxybenzoate (X) with a chiral 2-haloalkanol. This method is exemplified by the synthesis of 4'-n-decyloxyphenyl-4-[(4-methyl-2S-fluoro)pentyloxy]-3-fluorobenzoate (XVI, where $R_1$=decyloxy, $R_2$=isopropyl, and X and Z=F) as discussed in Example 3a.

To synthesize the enantiomer of the 4'-$R_1$-phenyl-4-[(2S -halo)alkoxy]-3-halobenzoates (XVI) produced by the method of Example 3a, the method of Scheme 4 is followed with the exception that the enantiomer of the 2-haloalkanol used previously (XV) is substituted for the 2-haloalkanol.

To synthesize chiral 4'-$R_1$-phenyl-4-[(1-methyl-2-halo)alkoxy]-3-halobenzoates (XXII), the method of Example 4a is followed. This method involves the coupling of an epoxy alkanol to 4'-$R_1$-phenyl-3-halo-4-hydroxybenzoate (X), the opening of the epoxy ring and the treatment of the resulting hydroxy group with a halogenating agent. This method is illustrated in Scheme 6 and is exemplified by the synthesis of 4'-n-decyloxyphenyl-4-[(1S,4-dimethyl-2S-fluoro)pentyloxy]-3-fluorobenzoate (XXII, where $R_1$=decyloxy, $R_2$=isopropyl, and X and Z=F).

To obtain 4'-n-decyloxyphenyl-4-[(1R,4-dimethyl-2R -fluoro)pentyloxy]-3-fluorobenzoate, the enantiomer of 4'-n -decyloxyphenyl-4-[(1S,4-dimethyl-2S-fluoro)pentyloxy]-3-fluorobenzoate, the procedure of Example 4a is followed with the exception that 1S,4-dimethyl-(2R,3R-epoxy)pentanol, the enantiomer of XIX ($R_2$=isopropyl), is used in place of compound XIX, as described in the Examples.

To obtain 4'-n-decyloxyphenyl-4-[(1R,4-dimethyl-2S -fluoro)pentyloxy]-3-fluorobenzoate, a diastereomer of 4'-n -decyloxyphenyl-4-[(1S,4-dimethyl-2S-fluoro)pentyloxy]-3 -fluorobenzoate, the method of Example 4a is followed with the exception that a compound of formula XVII, a diastereomer of formula XIX, is used in place of the compound of formula XIX.

To synthesize the chiral 4'-$R_1$-phenyl-4-[(1-methyl-2,3-difluoro)alkoxy]-3-halobenzoates, the procedure of Example 5a as illustrated by Scheme 7 is followed. This method involves the coupling of an epoxy alkanol (compound of formula XIX) to 4'-$R_1$-phenyl-3-halo-4-hydroxybenzoate (X), the opening of the epoxy ring and the treatment of the resulting compound with a halogenating agent. This method is exemplified by the synthesis of 4'-decyloxyphenyl-4-[(1S,4-dimethyl-2R,3R -difluoro)pentanyloxy]-3-fluorobenzoate (MDW 205) (XXV, where $R_1$=decyloxy, X, Y and Z=F and $R_2$=isopropyl), described in the Examples.

To obtain 4'-decyloxyphenyl-4-[(1R,4-dimethyl-2S,3S difluoro)pentyloxy]-3-fluorobenzoate, the enantiomer of 4'-decyloxyphenyl-4-[(1S,4-dimethyl-2R,3R-difluoro)pentanyloxy]-3-fluorobenzoate (MDW 205) (Example 5a), the method of Example 5a is followed with the exception that IS,4-dimethyl-(2R,3R -epoxy)pentanol is used in place of 1R,4-dimethyl-(2S,3S -epoxy)pentanol (XIX, where $R_2$=isopropyl).

The diastereomers of 4'-decyloxyphenyl-4-[(1S,4-dimethyl -2R,3R difluoro)pentanyloxy]-3-fluorobenzoate (MDW 205) can be synthesized by known methods from readily available starting materials, as exemplified by the synthesis of 4'-decyloxyphenyl-4-[1R,4-dimethyl-2R,3R-difluoro)pentanyloxy]-3-fluorobenzoate (MDW235), as described in the Examples.

As is understood by those of skill in the art, the agents used in the methods described herein for opening the epoxy ring and for halogenating the resulting hydroxy group can be replaced by alternate agents to produce compositions in which X and/or Y=chloride or other halogens, or to produce compositions in which X is a different halide from Y. For example, opening the epoxy ring with HCl rather than (HF)$_x$·pyridine results in a chlorohydrin rather than a fluorohydrin; treating the resulting hydroxy group With a halogenating agent, DAST, produces a chlorofluoro alkoxy proximal segment. However, treating the hydroxy group with chlorinating agent produces a dichloro alkoxy proximal segment.

As is also understood by those of skill in the art, the 2-haloalkanol used to produce the 2-haloalkoxy chiral proximal segment of compound formula XVI can comprise any halide, but preferably fluorine or chlorine.

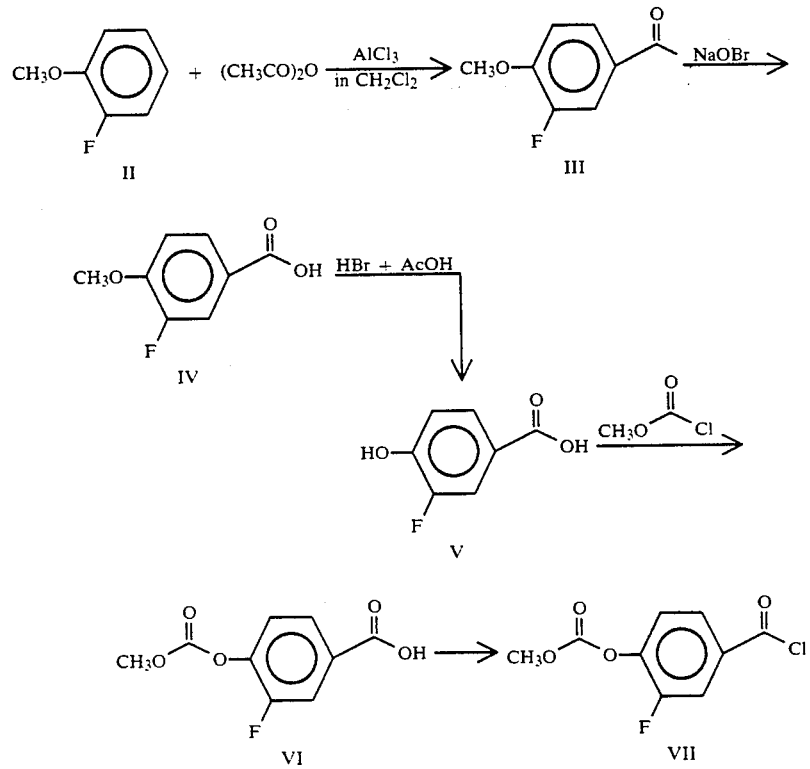

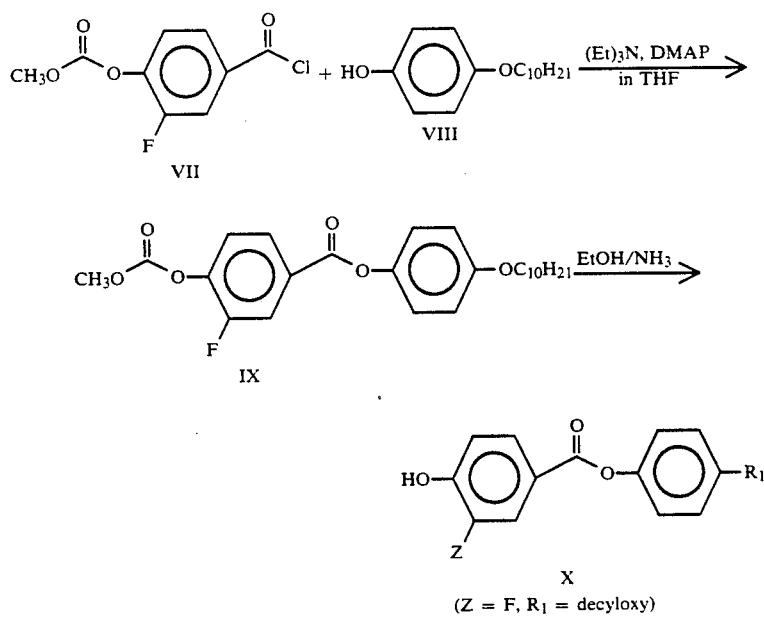

SCHEME 3:
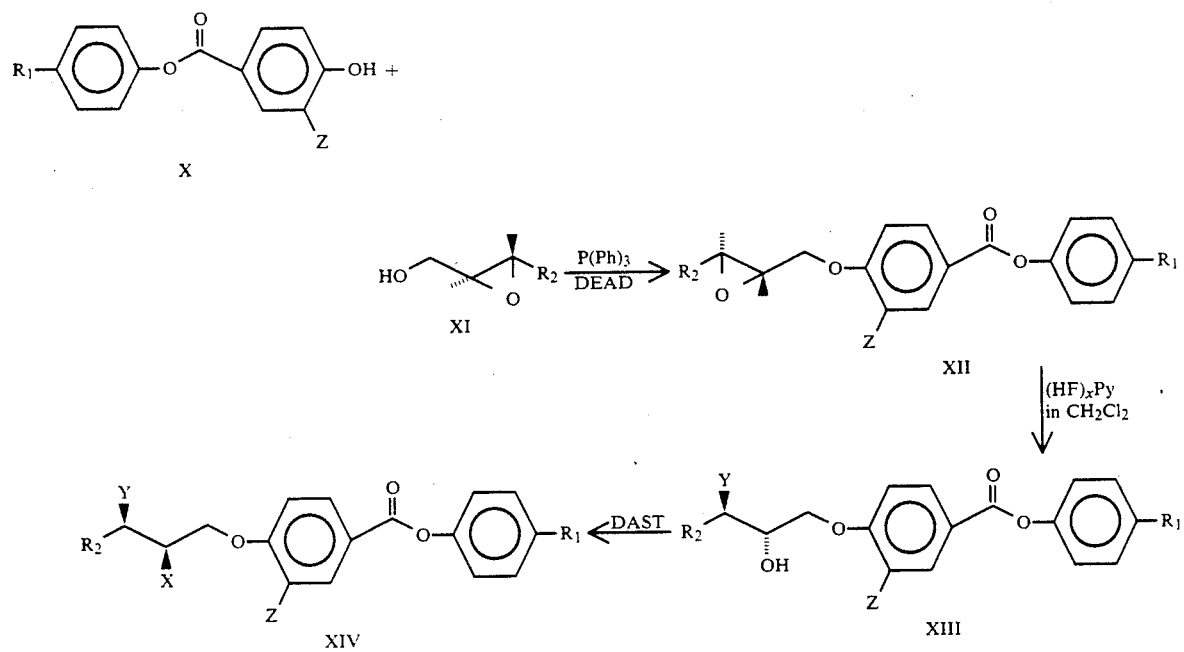
SCHEME 4:
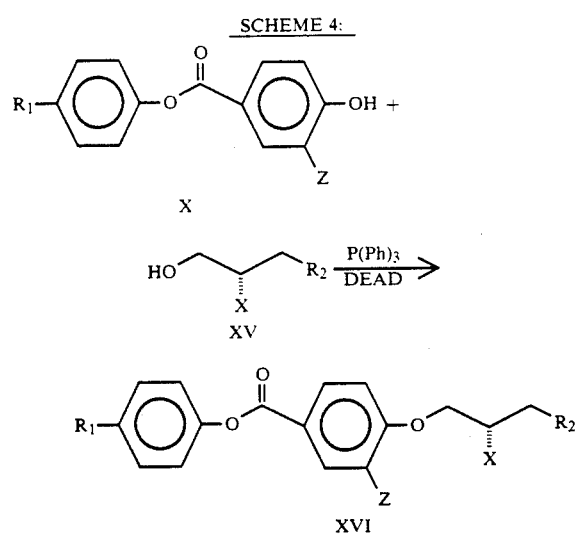
SCHEME 5:
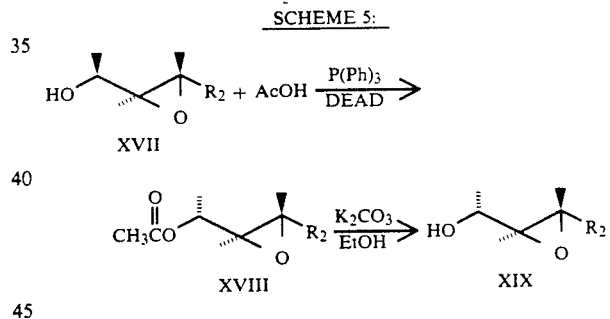
SCHEME 6:
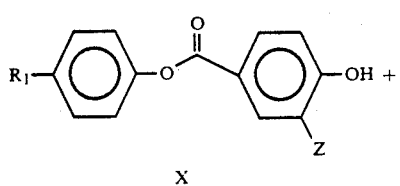

-continued
SCHEME 6:

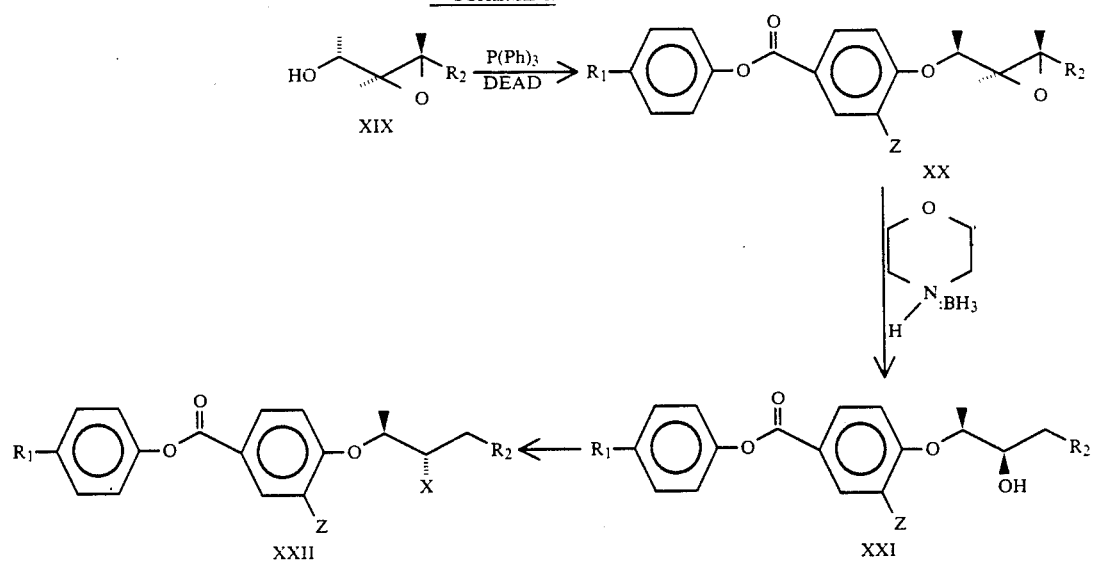

SCHEME 7:

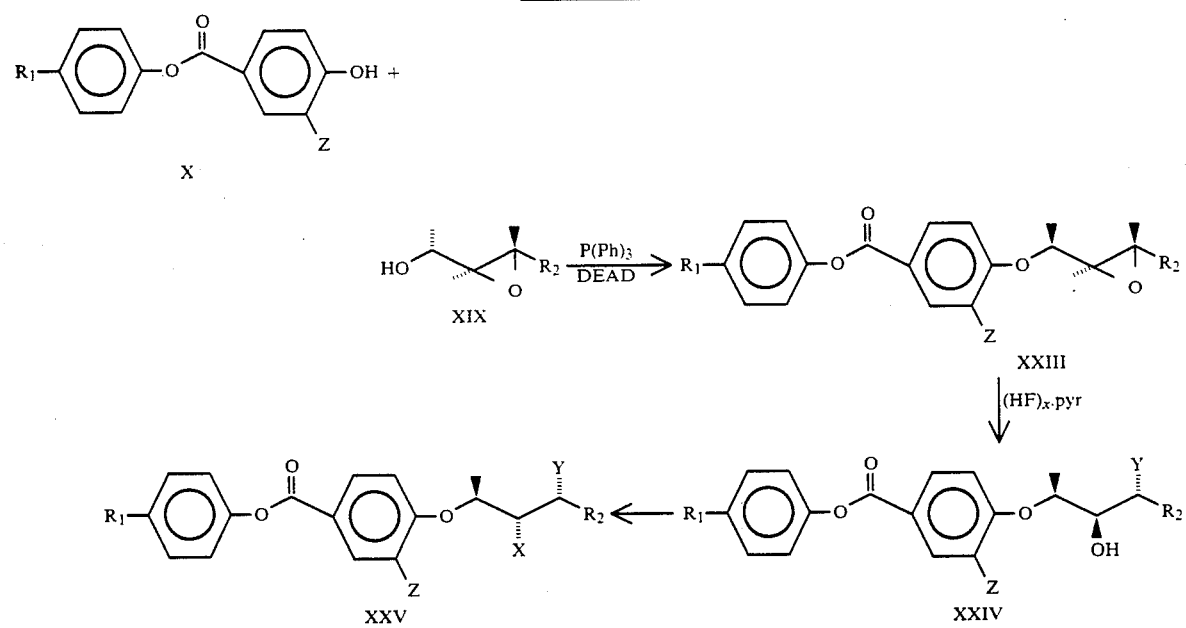

Many of the compounds of the subject invention, including compounds 4'-decyloxy-4-[(2S-fluoro-4-methyl)pentyloxy]-3-fluorobenzoate (general formula XVI), 4,-decyloxy-4-[(1S,4-dimethyl-2S-fluoro)pentyloxy]-3-fluorobenzoate (general formula XXII), 4'-decyloxy-4-[(2R,3R-difluoro)hexyloxy]-3-fluorobenzoate (general formula XIV), and 4'-decyloxy-4-[(1S,4-dimethyl-2R,3R-difluoro)pentyloxy]-3-fluorobenzoate (general formula XXV) of Table 2, do not possess an enantiotropic or monotropic ferroelectric (smectic C*) liquid crystal phase. However, when these compounds are mixed with a known FLC host material, such as W82, mixtures are produced which possess ferroelectric smectic C* phases and improved polarization density relative to that of the host material alone.

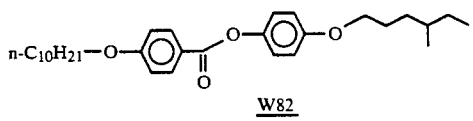

W82

Table 2 summarizes the polarization density and phase sequence temperatures of 10% (w/w) mixtures of subject compositions with W82. In Table 2, the phases are noted as X=crystal, I=isotropic liquid, A=smectic A, C=smectic C, F*=smectic F, N*=chiral nematic, and phase sequence temperatures are given in C. Spontaneous polarization densities ($P_s$) are given in nC/cm$^2$ and the magnitude of $P_s$ was measured by integration of the dynamic current response on reversing the applied electric field, as described in Martinot-Lagarde (1976) J. Phys. 37, C-3, p.129 and Martinot-Lagarde (1977) J. Phys. Lett. 38, L-17. $P_{s(ext)}$ is the polarization density for the subject compositions as extrapolated from a 10% by weight mixture of a subject composition in W82.

W82 is known to possess an enantiotropic ferroelectric C* phase with very low polarization density of about $-1$ nC/cm$^2$. Mixtures of the compounds of the present invention, particularly compounds as shown in Table 2, possess ferroelectric C* phases with higher polarization densities than W82 alone.

Compositions of the subject invention can also be mixed with host materials in any desired weight percentage. Generally, as the weight percentage of subject compositions in the host material is increased, polarization density of the FLC mixture increases linearly. Depending on the intended application, a person of skill in the art can determine the desired polarization of the FLC mixture and calculate the appropriate concentration of subject compositions in a host material to obtain the desired polarization in the mixture. Because the polarization densities of the subject applications are high, low concentrations are typically used as dopants to obtain the desired polarization in the mixture. Generally, the concentrations of the dopants used in the host are less than about 20% (w/w). Such low concentrations avoid orientational viscosity that may be associated with the use of higher concentrations of such dopants.

Generally, as dopant concentration in FLC mixture increases, the phase diagram of the mixture and the pitch may be altered. However, a person of skill in the art would be able to compensate for these effects.

Compositions of the subject invention can be mixed with any suitable host material. Suitable host materials vary with the intended application, but generally, solubility or miscibility with the dopant, broad C* phase temperature range (e.g., $-20°$ C. to $60°$ C.) and low orientational viscosity are considered desirable.

The polarization densities of FLC mixtures comprising the subject dopants can be greater than that of mixtures comprising analogous dopants not having a halogenated core and halogenated chiral tail, such as 4-decyloxyphenyl-4'-(1-methylhexyloxy)benzoate. More specifically, 4-decyloxyphenyl-4'-(1-methylhexyloxy)-benzoate has a $P_{s(ext)}$ of $-42$ nC/cm$^2$. As can be seen from Table 2, each of the exemplified compositions has a $P_{s(ext)}$ equal to or greater than that of 4-decyloxyphenyl-4'-(1-methylhexyloxy)-benzoate.

Table 2 also includes polarization, tilt angle and phase sequence data for compounds analogous to compositions of the subject invention, i.e., compounds not having halide(s) on the core. As can be seen from Table 2, the addition of a halide to the aromatic ring of the core adjacent to the chiral tail can improve the polarization density. It is believed that this improved polarization density of the subject compositions can be due in some cases to the relative alignment of the individual dipole moments of the halide bond(s) on the core with the dipoles of the oxygen and halide bond(s) on the proximal segment of the chiral tail. More specifically, the dipoles of the core halide bond(s) and the proximal segment oxygen and halide bond(s) are believed in some of the subject compositions to be in relative alignment with each other and substantially normal to the tilt plane in an FLC mixture C* phase.

TABLE 2

Phase sequence polarization and tilt angle data for C* mixtures using W82 as a host and containing 10% (w/w) of subject compositions.

| | Phase Sequence °C. | $P_s$ | Tilt Θ | $P_{s(ext)}$ | $P_{s(ext)} \div \sin Θ$ |
|---|---|---|---|---|---|
| MDW 186<br>4'-decyloxyphenyl-4-(2-fluoro-4-methyl)pentyloxybenzoate | I $\xrightarrow{73.3}$ N* $\xrightarrow{72.3}$ A $\xrightarrow{68}$ C* $\xrightarrow{28}$ X | −2.29 | 25 | −14 | −33 |
| MDW 187 (XVI)<br>4'-decyloxyphenyl-4-[(2S-fluoro-4-methyl)pentyloxy]3-fluorobenzoate | I $\xrightarrow{71.5}$ N* $\xrightarrow{70.5}$ A $\xrightarrow{68.1}$ C* $\xrightarrow{26}$ X | −5.06 | 28 | −42 | −89 |
| MDW 215<br>4'-decyloxyphenyl-4-(1,4-dimethyl-2-fluoro)pentyloxybenzoate | I $\xrightarrow{64.6}$ A $\xrightarrow{75.3}$ C* $\longrightarrow$ X | −8.39 | 25 | −75 | −177 |
| MDW 225 (XXII)<br>4'-decyloxyphenyl-4-[(1S,4-dimethyl-2S-fluoro)pentyloxy]-3-fluorobenzoate | I $\xrightarrow{61.5}$ A $\xrightarrow{55.2}$ C* $\xrightarrow{24.3}$ X | −9.85 | 29.5 | −90 | −183 |
| MDW 190<br>4'-decyloxyphenyl-4-(2,3-difluoro)hexyloxybenzoate | I $\xrightarrow{71.4}$ A $\xrightarrow{66.2}$ C* $\xrightarrow{33.5}$ X | −3.83 | 26.5 | −29 | −65 |
| MDW 199 (XIV)<br>4'-decyloxyphenyl-4-[(2R,3R-difluoro)hexyloxy]-3-fluorobenzoate | I $\xrightarrow{71.5}$ A $\xrightarrow{67.5}$ C* $\xrightarrow{24.5}$ X | −21.11 | 27.5 | −112 | −243 |

TABLE 2-continued

Phase sequence polarization and tilt angle data for C* mixtures using W82 as a host and containing 10% (w/w) of subject compositions.

| | Phase Sequence °C. | $P_s$ | Tilt $\Theta$ | $P_{s(ext)}$ | $P_{s(ext)} \div \sin \Theta$ |
|---|---|---|---|---|---|
| MDW 194<br>4'-decyloxyphenyl-4-<br>(1,4-dimethyl-2,3-<br>difluoro)pentyloxybenzoate | I $\xrightarrow{65.9}$ A $\xrightarrow{57.4}$ C* $\xrightarrow{18.3}$ F* $\xrightarrow{-2}$ X | −2.20 | 29.5 | −13 | −26 |
| MDW 205 (XXV)<br>4'-decyloxyphenyl-4-<br>[(1R,4-dimethyl-<br>2R,3R-difluoro)pentyloxy]- | I $\xrightarrow{65.8}$ A $\xrightarrow{57.6}$ C* $\xrightarrow{18.2}$ F* $\xrightarrow{-2}$ X | −7.66 | 29.0 | −68 | −140 |

As indicated hereinabove, compositions of the subject invention containing the following proximal segments are preferred:

| | |
|---|---|
| 2S-halo | 2R-halo |
| 1S-methyl-2S-halo | 1R-methyl-2R-halo |
| 2S,3S-dihalo | 2R,3R-dihalo |
| 1S-methyl-2R,3R-dihalo | 1R-methyl-2S,3S-dihalo. |

Compositions containing these proximal segments are preferred because they can have polarization densities greater than their diastereomers. For example, subject compositions comprising 1S-methyl-2S-halo or 1R-methyl-2R-halo proximal segments have polarization densities greater than their diastereomers having either 1R-methyl-2S-halo or 1S-methyl-2R-halo proximal segments. Subject compositions comprising 2S,3S-dihalo or 2R,3R-dihalo proximal segments have polarization densities greater than their diastereomers having either 2R,3S-dihalo or 2S,3R-dihalo proximal segments. Finally, subject compositions comprising 1S-methyl-2R,3R-dihalo or 1R-methyl-2S,3S-dihalo proximal segments have polarization densities greater than their diastereomers having 1R-methyl-2R,3R-dihalo, 1S-methyl -2S,3S-dihalo, 1S-methyl-2S,3R-dihalo, 1R-methyl-2R,3S-dihalo, 1S-methyl-2R,3S-dihalo, or 1R-methyl-2S,3R-dihalo proximal segments.

It is believed that the subject compositions comprising the preferred proximal segments have greater polarization densities relative to their respective diastereomers due to the relative alignment of the dipole moments of the core halide(s) and the oxygen and halide(s) of the proximal segment in the preferred compositions. The dipoles of the core halide(s) and oxygen and halide(s) of the proximal segment are believed to be in relative alignment and substantially normal to the tilt plane in an FLC composition smectic C* phase.

It should be noted that it is dipole orientation of the subject conformations in the oriented smectic C phase that affects polarization density. Only the components of the dipoles normal to the tilt plane affect polarization. The structure of the proximal and distal segments of the achiral tail and steric interaction between the groups will affect dipole orientation and the magnitude and sign of the polarization density. The relationship between dipole alignment and ferroelectric polarization density has been discussed for related molecules in Walba et al. (1986) J. Amer. Chem. Soc. 108:5210–5221 and Walba et al. (1986) J. Amer. Chem. Soc. 108:7424–7425, both of which are incorporated herein by reference.

The subject invention further comprises a method for distinguishing the compositions comprising the preferred proximal segments from their respective diastereomers. This method is based on the greater polarization density of a preferred composition relative to its diastereomers. For example, a sample of 4-decyloxyphenyl-4'-[(1S,4-dimethyl-2R,3R -difluoro)pentyloxy]-3-fluorobenzoate can be distinguished from a sample of 4-decyloxyphenyl-4'-[(1R,4-dimethyl-2R,3R -difluoro)-pentyloxy]-3-fluorobenzoate by the greater polarization density of the former.

The method for distinguishing a preferred composition from one of its diastereomers comprises the steps of:

(a) measuring the polarization density of samples of each isomer, and (b) selecting the composition having the greatest polarization density.

The isomer having the larger polarization density is the composition having the preferred proximal segment.

It is believed that the composition selected by this selection method has a greater polarization density because the dipole moments of its core halide(s) and proximal segment oxygen and halide(s) bonds are relatively aligned substantially normal to the tilt plane in an FLC composition smeotic C* phase. For example, 4-decyloxyphenyl-4'-[(1S,4-dimethyl-2R,3R -difluoro)pentyloxy]3-fluorobenzoate has a greater polarization density than its diastereomer, 4-decyloxyphenyl-4'-[(1R,4-dimethyl-2R,3R-difluoro)pentyloxy]-3-fluorobenzoate, due to the relative alignment of the dipoles of the core fluoride and proximal segment oxygen and fluorides.

The subject invention also comprises a method for selecting subject compositions having an absolute polarization density greater than about 1 nC/cm². As used herein "absolute polarization density greater than about 1 nC/cm²" means a polarization density having a positive numerical value greater than about +1 nC/cm² or a negative numerical greater than about −1 nC/cm², e.g., −5 nC/cm².

The method for selecting subject compositions having an absolute polarization density greater than about 1 nC/cm² comprises the steps:

(a) synthesizing subject compositions comprising an ortho or ortho and meta halogenated core and a 1-methyl-2-haloalkoxy, 2-haloalkoxy, 2,3-haloalkoxy or 1-methyl-2,3-dihaloalkoxy proximal segment by methods described herein, (b) measuring the polarization densities of the compositions synthesized in (a) by methods described herein, (c) selecting from the compositions of step (b) those compositions having an absolute polarization density greater than about 1 nC/cm².

As described herein, because many of the subject compositions in pure form do not have a smectic C phase, the polarization density of a particular composition can be assigned by extrapolating the polarization value of an FLC mixture, e.g., a 10% by weight mixture of the dopant in W82, to a theoretical polarization value based on a 100% dopant composition and an assumed C phase for the dopant. The terms "absolute polarization density" and "polarization density" are meant to include such extrapolated polarizations.

EXAMPLES

Example 1

Synthesis of 4'-$R_1$-phenyl-3-halo-4-hydroxy benzoates (X)

This example illustrates the synthesis of 4'-$R_1$-phenyl-3-halo-4-hydroxy benzoates, which can be used in the remaining Examples to produce phenyl halobenzoates having the chiral tails of the subject invention. The synthesis of 4'-$R_1$-phenyl -3-halo-4-hydroxy benzoates is illustrated by the synthesis of 4'-decyloxyphenyl-3-fluoro-4-hydroxybenzoate (X, where $R_1$=decyloxy and Z=F) described hereinbelow and illustrated in Schemes 1 and 2.

Initially, 2-fluoroanisole (II) was used to synthesize 3-fluoro-4-methoxyacetophenone (III). $AlCl_3$ (0.6 mol) and acetic anhydride (0.4 mol) were placed in 250 ml of dry dicloromethane. The 2-fluoroanisol (0.2 mol) was added dropwise over a period of 30 minutes to the reaction mixture which was then stirred with a magnetic stir bar for two hours. The reaction was judged complete by TLC. The reaction mixture was then poured in ice and stirred for one hour. The $CH_2Cl_2$ layer was separated and the water layer was extracted twice with $CH_2Cl_2$. Organic layers were combined and washed with 3N HCl and water, dried with $MgSO_4$ and passed through a thick pad of silica. The solvent was rotary evaporated to obtain the crude product, which was crystallized from 7% (v/v) ethyl acetate in hexanes to obtain 70% yield of the crystallized product, 3-fluoro-4-methoxyacetophenone (III).

3-fluoro-4-methoxyacetophenone (11.5 g) was dissolved in 100 ml dioxane and NaOBr solution (as prepared below) was added dropwise, with constant stirring with a stir bar at room temperature. The NaOBr solution was prepared by dissolving 40 g of NaOH in 500 ml of water, cooling to 0° C. in an ice bath, and adding bromine (12.5 ml) dropwise while stirring with stir bar; bromine was added slowly so that the reaction mixture did not exceed 5° C. After overnight stirring of the 3-fluoro-4-methoxyacetophenone, dioxane and NaOBr solution, the reaction mixture was diluted with water (200 ml). Since the reaction mixture was basic, the product, benzoic acid, was in water as its sodium salt. The resultant mixture was partitioned between ether and water. The ether layer was washed with dilute aqueous NaOH to extract any remaining product as Na salt. The aqueous layers were combined and acidified to pH 1 to precipitate the benzoic acid. The resulting acid was extracted with ether. The ether layer was washed with water a few times, dried with $MgSO_4$, and filtered. Rotary evaporation of the ether fraction afforded 3-fluoro-4-methoxybenzoic acid (IV) in 85% yield.

Next, the 3-fluoro-4-methoxybenzoic acid (IV) was digested with HBr (20 ml) and glacial acetic acid (40 ml) overnight. Most of the acetic acid was distilled off and the remaining mixture was diluted with water. The precipitated benzoic acid was extracted in ether; the ether layer was dried, filtered and rotary evaporated to produce 11.0 g of the 3-fluoro-4-hydroxybenzoic acid (V).

4-methoxycarbonyloxy-3-fluorobenzoic acid (VI) was synthesized from 3-fluoro-4-hydroxybenzoic acid (V) by reaction of the latter with methyl chloroformate. NaOH (90 mmol) and 3-fluoro-4-hydroxybenzoic acid (30 mmol) were dissolved in water (80 ml) and cooled to −20° C. Methyl chloroformate (45 mmol) was added dropwise to the mixture. The mixture was then stirred with a magnetic stir bar at 5° C. for four hours and left overnight in the refrigerator. The mixture was then acidified to pH 5 to precipitate 4-methoxycarbonyloxy-3-fluorobenzoic acid. The precipitates were filtered and crystallized from acetonitrile to afford the clean product, 4-methoxycarbonyloxy -3-fluorobenzoic acid (VI), in a 77% yield.

To produce 4-methoxycarbonyloxy-3-fluorobenzoyl chloride (VII), the 4-methoxycarbonyloxy-3-fluorobenzoic acid (VI) (2.4 mmol) was refluxed overnight in neat oxalylchloride; excess oxalylchloride was removed under vacuum and traces of it were removed under high vacuum. The 4-methoxycarbonloxy-3-fluorobenzoyl chloride (2.4 mmol) (VII) and 4-decyloxyphenol (VIII) (2.4 mmol) were dissolved in dry cold (0° C.) THF. Triethylamine (8 mmol) was added dropwise, followed by a catalytic amount of DMAP. The reaction mixture was then stirred with a magnetic stir bar for three hours at room temperature. The solvent was then rotary evaporated until dryness and the residue was passed through a thick pad of silica using 20% (v/v) hexanes in $CH_2Cl_2$. The solvent was taken off under vacuum to obtain the produce, 4'-n -decyloxyphenyl-4-methoxycarbonyloxy-3-fluorobenzoate (IX), in 80% yield.

1.92 mmol of the 4'-n-decyloxyphenyl-4-methoxycarbonyloxy -3-fluorobenzoate (IX) was dissolved in 50 ml of ethanol and 2 ml of aqueous 30% $NH_3$ (v/v) was added to it. The reaction mixture was stirred for 30 minutes with a magnetic stir bar. After the reaction was complete, the solution was poured into water and cooled in dry ice. The precipitate product was filtered and recrystallized from acetonitrile to afford 4'-decyloxyphenyl-(4-hydroxy-3-fluoro)benzoate (X, where $R_1$=decyloxy and Z=F) in 85% yield.

Example 1a

Other 4'-$R_1$-4-hydroxy Substituted Cores Useful in Synthesis of Subject Compositions Other 4'-$R_1$,4-hydroxy substituted cores are either commercially available or can be synthesized by known methods from readily available starting materials. A variety of achiral tails, i.e., alkyl, alkenyl or alkoxy that are straight chain or branched, or have other variations as described hereinabove, can be appended by known methods to the core 4' relative to the 4-hydroxy substitution on the core. Further, cores having o-halo or o,m-dihalo substitution relative to the 4-hydroxy substitution are commercially available or can be synthesized by known methods from readily available starting materials. These other 4'-$R_1$,4-hydroxy substituted cores can be used in the methods of the remaining Examples.

Example 2

Synthesis of Chiral 4'-R$_1$-phenyl-4-[(2,3-dihalo)alkoxy]-3-halobenzoates (XIV)

This example illustrates the synthesis of nonracemic chiral 4'-R$_1$-phenyl-4-[(2,3-dihalo)alkoxy]-3-halobenzoates by stereospecific (or selective) halogenation of chiral phenylbenzoate epoxides. These syntheses proceed through 2,3 halohydrin intermediates. The procedure is illustrated by the synthesis of the trifluoride, 4'-n-decyloxyphenyl-4-[(2R,3R -difluoro)hexyloxy]-3-fluoro-benzoate (XIV, where R$_1$=decyloxy, X, Y and Z=F, and R$_2$=propyl).

Example 2a

Synthesis of 4'-n-decyloxyphenyl-4-(2R,3R -difluoro)hexyloxy-3-fluoro-benzoate 2.1 mmol of 4'-decyloxyphenyl-4-hydroxy-3-fluorobenzoate (X, where R$_1$=decyloxy and Z=F), 2.3 mmol of (2S,3S -epoxy)hexanol (XI, where R$_2$=propyl), and 3 mmol of triphenylphosphine were dissolved in 10 ml of dry THF. A solution of diisopropyl azodicarboxylate (DEAD) (3 mmol) in 1 ml of dry THF was added dropwise over a period of two hours. The reaction mixture was stirred for two hours with a magnetic stir bar. The solvent was then taken off under vacuum and the residue was flash chromatographed (silica gel column) using 5% (v/v) ethyl acetate in hexanes as eluent to afford the (2S,3S) epoxy product, 4'-decyloxyphenyl-4-[(2S,3S-epoxy)hexyloxy]-3-fluorobenzoate (XII, where R$_1$=decyloxy, Z=F, R$_2$=propyl), in 44% yield.

120 mg of 4'-decyloxyphenyl-4-[(2S,3S-epoxy)hexyloxy]-3-fluorobenzoate was then dissolved in 10 ml of dry CH$_2$Cl$_2$ and cooled to 0° C. 0.5 ml of hydrogen fluoride in pyridine was added to the cold solution and stirred with a magnetic stir bar for one hour. The reaction was judged complete by TLC. The reaction was then quenched by the addition of cold water and stirring with a magnetic stir bar for 15 minutes. The solvent was rotary evaporated and the residue was flash chromatographed on a silica column using 10% (v/v) ethyl acetate in hexanes to obtain 72.8% yield of the fluorohydrin product, XIII where R$_1$=decyloxy, X and Z=F and R$_2$=propyl.

In a flame dried argon filled flask, the fluorohydrin product (0.25 mmol) was dissolved in 20 ml of dry CH$_2$Cl$_2$ and cooled to −70° C. 0.1 ml of dimethylaminosulfurtrifluoride (DAST) was added to the reaction mixture and was allowed to stir with a magnetic stir bar for two hours at −70° C. The reaction mixture was stored in the refrigerator overnight. The reaction was quenched by addition of cold NaHCO$_3$ solution and stirring with a magnetic stir bar for 15 minutes. The product was extracted twice with 50 ml portions of CH$_2$Cl$_2$. Organic layers were combined and washed repeatedly with NaHCO$_3$ solution and brine, dried with MgSO$_4$, filtered and rotary evaporated. The residue was flash chromatographed on a silica column using 5% (v/v) ethyl acetate in hexanes to obtain 79% yield. The final product, 4'-decyloxyphenyl-4-[(2R,3R-difluoro)hexyloxy]-3-fluorobenzoate (XIV, where R$_1$=decyloxy, X, Y and Z=F, and R$_2$=propyl) was further purified by crystallization from hexanes.

Example 2b

Synthesis of 4'-decyloxyphenyl-4-[(2S,3S -difluoro)hexyloxy]-3-fluorobenzoate The synthesis of 4'-decyloxyphenyl-4-[(2S,3S -difluoro)hexyloxy]-3-fluorobenzoate is accomplished by following the same method of Example 2a with the exception that (2R,3R-epoxy)hexanol is used in place of its enantiomer, (2S,3S-epoxy)hexanol (XI, where R$_2$=propyl).

Example 2c

Synthesis of 4'-decyloxyphenyl-4-[(2R,3S -difluoro)hexyloxy]-3-fluorobenzoate The synthesis of 4'-decyloxyphenyl-4-[(2R,3S -difluoro)hexyloxy]-3-fluorobenzoate, the diastereomer of 4'-decyloxyphenyl-4-[(2R,3R-difluoro)hexyloxy]-3-fluorobenzoate (Example 2a), can be accomplished by following the method of Example 2a with the exception that (2S,3R-epoxy)hexanol, a diastereomer of (2S,3S-epoxy)hexanol (XI, where R$_2$=propyl), is used in place of XI.

An alternate route of obtaining 4'-decyloxyphenyl-4-[(2R,3S -difluoro)hexyloxy]-3-fluorobenzoate follows. Initially, 4-decyloxyphenyl-4-[(2S,3S-epoxy)hexyloxy]-3-fluorobenzoate is synthesized by coupling p-decyloxyphenol with 4-[(2S,3S -epoxy)hexyloxy]-3-fluorobenzoyl chloride. Decyloxyphenol and 4-[(2S,3S-epoxy)hexyloxy]-3-fluorobenzoyl chloride are commercially available or can be synthesized by known methods from readily available starting materials. The p-decyloxyphenol is mixed with 4-[(2S,3S-epoxy)hexyloxy]-3-fluorobenzoyl chloride, dry methylene chloride, triethylamine and a few crystals of DMAP. The resulting mixture is stirred for 1 hour, after which the solvent is removed in vacuo. The residue is treated with aqueous HCl (5%, v/v) followed by extraction with ether. The combined ether layers are then washed sequentially with 5% aqueous HCl, 5% aqueous NaOH, and water and dried over anhydrous sodium sulfate. Removal of the solvent gives the crude intermediate product, 4-decyloxyphenyl -4-[(2S,3S-epoxy)hexyloxy]-3-fluorobenzoate, which can then be purified by flash chromatography using 9:1 (v/v) hexanes:ethyl acetate as eluent. The product can be further purified by recrystallization from ethanol.

Next, the 4-decyloxyphenyl-4-[(2S,3S-epoxy-hexyloxy]-3-fluorobenzoate is dissolved in methylene chloride, and the reaction solution cooled to 0° C. (HF)$_x$·pyridine is added and the resulting mixture is stirred for 15 minutes. The reaction is then quenched with water. Ethereal extractive workup results in a mixture of the fluorohydrin regioisomers.

The mixture of fluorohydrin regioisomers is dissolved in dry methylene chloride and cooled to −78° C., under argon. Diethylaminosulfurtrifluoride (DAST) is added dropwise to the cooled solution which is then stirred for ten minutes. The cooling bath is then removed after which the reaction is stirred for an additional hour. The reaction is then quenched with 10% (w/v) sodium bicarbonate. An ethereal extractive workup results in a mixtures of the diastereomers: the 2R,3R -difluoride and the 2R,3S-difluoride. The diastereomeric difluorides can then be separated and purified by flash chromatography on a silica gel (ethyl acetate:hexanes, 8%, v/v) in two fractions. The first fraction is the 2R,3S-difluoride, 4'-decyloxyphenyl-4-

[(2R,3S-difluoro)hexyloxy]-3-fluorobenzoate. The second fraction is the 2R,3R-difluoride.

Example 3

Synthesis of 4'-R$_1$-phenyl-4-[(2-halo)alkoxy]-3-halobenzoates (XVI)

This example illustrates the synthesis of chiral non-racemic 4'-R$_1$-phenyl-4-[(2-halo)alkoxy]-3-halobenzoates (XVI) by the coupling of 4'-R$_1$-phenyl-3-halo-4-hydroxybenzoates with chiral 1-hydroxy-2-haloalkyls. The procedure is exemplified by the synthesis of the difluoro, 4'-n-decyloxyphenyl-4-[(4-methyl -2S-fluoro)-pentyloxy]-3-fluorobenzoate (XVI, where R$_1$=decyloxy, X and Z=F, and R$_2$=isopropyl).

Example 3a

Synthesis of 4'-n-decyloxyphenyl-4-[(4-methyl-2S-fluoro)pentyloxy]-3-fluorobenzoate To produce 4'-n-decyloxyphenyl-4-[(4-methyl-2S-fluoro) pentyloxy]-3-fluorobenzoate, 4'-decyloxyphenyl-(4-hydroxy-3-fluoro)benzoate (X, where R$_1$=decyloxy and Z=F), 4-methyl -2S-fluoropentanol (XV, where X=F and R$_2$=isopropyl) (0.5 mmol) and triphenyl phosphine (0.75 mmol) were dissolved in dry THF and stirred with a magnetic stir bar for five minutes. Diisopropyl azodicarboxylate (1.5 equivalents) dissolved in dry THF, was allowed to drop in the reaction mixture at room temperature over a period of two hours. The reaction was further stirred with a stir bar overnight. The solvent was then rotoevaporated to dryness and the residue was subjected to flash chromatography on a silica column using 10% (v/v) ethyl acetate in hexanes to afford the product, 4'-n -decyloxyphenyl-4-[(4-methyl-2S-fluoro)pentyloxy]-3-fluorobenzoate in 84.3% yield. The product was further purified by crystallization from hexanes.

Example 3b

Synthesis of 4'-n-decyloxyphenyl-4-[(4-methyl-2R-fluoro)pentyloxy]-3-fluorobenzoate To synthesize 4'-n-decyloxyphenyl-4-[(4-methyl-2R-fluoro)pentyloxy]-3-fluorobenzoate (XVI, where R$_1$=decyloxy, X and Z=F, and R$_2$=isopropyl), the method for Example 3b is followed with the exception that 4-methyl-2R-fluoropentanol is used in place of its enantiomer 4-methyl-2S-fluoropentanol (XV, where R$_2$=isopropyl).

Example 4

Synthesis of 4'-R$_1$-phenyl-4-[(1-methyl-2-halo)alkoxy]-3-halobenzoates

This example illustrates the synthesis of chiral non-racemic 4'-R$_1$-phenyl-4-[(1-methyl-2-halo)alkoxy]-3-halobenzoates (XXII) by coupling of 4'-R$_1$-phenyl-3-halo-4-hydroxybenzoate (X) with a chiral 1-methyl-(2,3-epoxy)alkanol, opening the epoxy ring, followed by stereospecific halogenation of the resulting hydroxy group. The procedure is illustrated by the synthesis of the difluoride, 4'-n-decyloxyphenyl-4-[(1S,4-dimethyl-2S -fluoro)pentyloxy]-3-fluorobenzoate (XXII, where R$_1$=decyloxy, X and Z=F, and R$_2$=isopropyl) as illustrated by Scheme 6.

Example 4a

Synthesis of 4'-decyloxyphenyl-4-[(1S,4-dimethyl-2S-fluoro)pentyloxy]-3-fluorobenzoate To produce 4'-decyloxyphenyl-4-[1S,4-dimethyl-(2S, 3S-epoxy)pentyloxy]-3-fluorobenzoate (XX, where R$_1$=decyloxy, Z=F and R$_2$=isopropyl), 0.64 mmol of 4'-decyloxyphenyl-(4-hydroxy-3-fluoro)benzoate (X, where R$_1$=decyloxy and Z=F), 0.65 mmol of 1R,4-dimethyl-(2S,3S-epoxy)-pentanol (XIX, where R$_2$=isopropyl) and triphenylphosphine were dissolved in dry THF in an argon filled flask. 1R,4-dimethyl-(2S,3S-epoxy)-pentanol was produced by the Mitsunobu reaction described in Example 4b. Diisopropyl azodicarboxylate dissolved in dry THF was added dropwise over a period of two hours while the mixture was stirred with a stir bar. The reaction mixture was further stirred overnight. The solvent was then rotoevaporated and the residue was subjected to flash chromatography on a silica column using an eluent of 5% (v/v) ethyl acetate in hexanes to afford the product, 4'-n-decyloxyphenyl-4-[1S,4-dimethyl -(2S,3S-epoxy)-pentyloxy]-3-fluorobenzoate (XX, where R$_1$=decyloxy, Z=F and R$_2$=isopropyl), in a 50% yield.

110 mg of 4'-decyloxyphenyl-4-[1S,4-dimethyl-(2S,3S-epoxy) -pentyloxy]-3-fluorobenzoate was dissolved in dry CH$_2$Cl$_2$ in an argon filled flask and cooled to 0° C. Morpholine borane complex (40 mg) and BF$_3$-Et$_2$O (0.1 ml) were added and stirred with a stir bar for four hours until disappearance of the starting material. The reaction was then quenched with water and stirred for one hour at room temperature with a magnetic stir bar. Water (50 ml) was added and the organic layer was separated. The water layer was extracted twice with CH$_2$Cl$_2$. The combined organic layers were washed with brine, dried with MgSO$_4$, filtered and rotoevaporated. The residue was flash chromatographed with an eluent of 20% (v/v) ethyl acetate in hexanes on a silica column to afford 4'-decyloxyphenyl-4-[(1S,4-dimethyl-2R-hydroxy)pentyloxy]-3-fluorobenzoate (XXI, where R$_1$=decyloxy, Z=F and R$_2$=isopropyl) in 80% yield.

4'-decyloxyphenyl-4-[(1S,4-dimethyl-2R-hydroxy)-pentyloxy]-3-fluorobenzoate (85 mg) was dissolved in dry CH$_2$Cl$_2$ in a flame dried, argon filled flask and cooled to −70° C. Dimethylaminosulfurtrifluoride (DAST) (0.1 ml) was added to the cold solution. The reaction was stirred at −70° C. with a stir bar for four hours and then warmed to room temperature while stirring over a period of eighteen hours. The reaction was then quenched with cold NaHCO$_3$ solution and stirred for 15 minutes. The product was extracted with two 50 ml portions of CH$_2$Cl$_2$. Organic layers were combined and washed repeatedly with NaHCO$_3$ solution and brine, dried with MgSO$_4$, filtered and rotoevaporated. The residue was flash chromatographed on a silica column using 5% (v/v) ethyl acetate in hexanes to obtain the 20% yield of 4'-decyloxyphenyl-4-[(1S,4-dimethyl-2S-fluoro) pentyloxy]benzoate. The final product was further purified by crystallization from hexanes at −20° C.

Example 4b

Synthesis of 1R,4-dimethyl-(2S,3S-epoxy)-pentanol

The synthesis of 1R,4-dimethyl-(2S,3S-epoxy)-pentanol (XIX, where R$_2$=isopropyl) is illustrated by Scheme 5. The epoxy alcohol, 1S,4-dimethyl-(2S,3S- epoxy)pentanol, (XVII, where $R_2$=isopropyl) (7.7 mmol), acetic acid (8 mmol) and triphenylphosphine (16 mmol) were dissolved in dry THF and a solution of diisopropyl azodicarboxylate (16 mmol) in dry THF was added dropwise over a period of three hours while stirred with magnetic stir bar. The reaction mixture was stirred overnight. The solvent was rotoevaporated and the residue was subjected to flash chromatography on a silica column using 4% (v/v) ethyl acetate in hexanes as eluent. The spot at $R_f$ 0.46 was collected in 50% yield. TLC resulted in two spots, $R_f$ 0.54 and 0.46. The second spot at $R_f$ 0.46 is the major product, the epoxy acetate of XVIII, where $R_2$=isopropyl. Since both spots are very close it is hard to completely separate the two diastereomers in a single flash chromatography procedure, although the overall yield of the epoxy acetate was high (86%).

The inverted acetate (200mg) was dissolved in methanol (2 ml). Anhydrous $K_2CO_3$ (50 mg) was added and stirred with a stir bar at room temperature for half an hour. The completion of the reaction was judged by TLC. The solvent was carefully rotoevaporated and the residue was partitioned between ether and water fractions. The water layer was extracted twice with ether. Ether layers were combined, washed with diluted brine, dried over $MgSO_4$, filtered and rotoevaporated to obtain the 1R,4-dimethyl-2S,3S-epoxy pentanol (XIX, where $R_2$=isopropyl).

Example 4c

Synthesis of 4'-decyloxyphenyl-4-[(1R,4-dimethyl -2R-fluoro)pentyloxy]-3-fluorobenzoate To synthesize 4'-decyloxyphenyl-4-[(1R,4-dimethyl-2R -fluoro)pentyloxy]-3-fluorobenzoate, i.e., the enantiomer of the composition produced by Example 4a, the method of Example 4a for the synthesis of 4'-decyloxyphenyl-4-[(1S,4-dimethyl-2S -fluoro)pentyloxy]-3-fluorobenzoate is followed with the exception that 1S,4-dimethyl-(2R,3R-epoxy)pentanol, the enantiomer of XIX ($R_2$=isopropyl), is used in place of compound XIX. The enantiomer of epoxy alcohol XIX can be synthesized by known methods from readily available starting materials.

Example 4d

Synthesis of 4'-decyloxyphenyl-4-[(1R,4-dimethyl -2S-fluoro)pentyloxy]-3-fluorobenzoate To synthesize 4'-decyloxyphenyl-4-[(1R,4-dimethyl-2S -fluoro)pentyloxy]-3-fluorobenzoate, the diastereomer of 4'-decyloxyphenyl-4-[(1S,4-dimethyl-2S-fluoro)-pentyloxy]-3-fluorobenzoate (Example 4a), the method of Example 4a is followed with the exception that 1S,4-dimethyl-(2S,3S -epoxy)pentanol, XVII where $R_2$=isopropyl, is used in place of compound XIX. Compounds of formula XVII can be synthesized by known methods from readily available starting materials.

Example 5

Synthesis of Chiral 4'-$R_1$-phenyl-4-[(1-methyl-2,3-difluoro)alkoxy]-3-halobenzoates (XXV)

To synthesize 4'-$R_1$-phenyl-4-[(1-methyl-2,3-dihalo)alkoxy]-3-halobenzoates, 4'-$R_1$-phenyl-4-hydroxy-3-halobenzoate (X) is coupled to a chiral 1-methyl-2-epoxy alkanol, the epoxy ring is opened and treated with a halogenating agent. The synthesis of 4'-$R_1$-phenyl-4-[(1-methyl-2,3-dihalo)alkoxy]-3-halobenzoates is exemplified by the synthesis of 4'-decyloxyphenyl-4-[(1S,4-dimethyl-2R,3R-difluoro)pentanyloxy]-3-fluorobenzoate (XXV, where $R_1$=decyloxy, X, Y and Z=F and $R_2$=isopropyl) as illustrated in Scheme 7.

Example 5a

Synthesis of 4'-decyloxyphenyl-4-[(1S,4-dimethyl -2R,3Rdifluoro)pentanyloxy]-3-fluorobenzoate (MDW 205)

4'-decyloxyphenyl-(4-hydroxy-3-fluoro)benzoate (0.77mmol), 1R,4-dimethyl-(2S,3S-epoxy)pentanol (XIX, $R_2$=isopropyl) (0.8 mmol) and triphenylphosphine (1.5 mmol) were dissolved in 10 ml of dry THF. A solution of DEAD (3 mmol) in 1 ml of dry THF was added dropwise over a period of two hours. The reaction mixture was stirred for two hours with a magnetic stir bar. The solvent was then taken off under vacuum and the residue was flash chromatographed using 5%.(v/v) ethyl acetate in hexanes as eluent to afford the 4'-decyloxyphenyl-4-[(1S,4-dimethyl -2S,3S-epoxy)pentanyloxy]-3-fluorobenzoate (XXIII, where $R_1$=decyloxy, Z=F and $R_2$=isopropyl) in 44% yield.

190 mg (0.38 mmol) of the 4'-decyloxyphenyl-4-[(1S,4-dimethyl-2S,3S-epoxy)pentanyloxy]-3-fluorobenzoate was dissolved in 10 ml of dry $CH_2Cl_2$ and cooled to 0° C. 0.5 ml of HF in pyridine was added to the cold solution and stirred for one hour (completion of reaction measured by TLC). It was then quenched with cold water and stirred further for 15 minutes. The solvent was rotary evaporated and the residue was flash chromatographed on a silica column using 10% (v/v) ethyl acetate in hexanes to obtain 91% of the fluorohydrin product (XXIV, where $R_1$=decyloxy, X and Z=F and $R_2$=isopropyl).

In a flame dried argon filled flask, the fluorohydrin product (0.35 mmol) from above reaction, was dissolved in 20 ml of dry $CH_2Cl_2$ and cooled to −70° C. 0.1 ml of dimethyl aminosulfurtrifluoride (DAST) was added to the reaction mixture and was allowed to stir for two hours at −70° C. The reaction mixture was stored in the refrigerator overnight. It was quenched with cold $NaHCO_3$ solution and stirred for 15 minutes. The product was extracted in $CH_2Cl_2$ (two 50 ml portions). Organic layers were combined and washed repeatedly with $NaHCO_3$ solution and brine, dried with $MgSO_4$, filtered and rotary evaporated. The residue was flash chromatographed on a silica column using 5% (v/v) ethyl acetate in hexanes to obtain 49% yield. The final product, 4'-decyloxyphenyl-4-[(1S,4-dimethyl -2R,3R-difluoro)pentanyloxy]-3-fluorobenzoate (XXV, where $R_1$=decyloxy, X, Y and Z=F and $R_2$=isopropyl), was further purified by crystallization from hexanes.

Example 5b

Synthesis of 4'-decyloxyphenyl-4-[(1R,4-dimethyl -2S,3S-difluoro)pentanyloxy]-3-fluorobenzoate To synthesize 4'-decyloxyphenyl-4-[(1R,4-dimethyl-2S,3S -difluoro)pentanyloxy]-3-fluorobenzoate, the procedure of Example 5a is followed with the exception that 1S,4-dimethyl -(2R,3R-epoxy)pentanol is used in place of 1R,4-dimethyl-(2S,3S -epoxy)pentanol (XIX, $R_2$=isopropyl). 1S,4-dimethyl-(2R,3R -epoxy)pentanol is commercially available or can be synthesized by known methods from readily available starting materials.

Example 5c

Synthesis of 4'-decyloxyphenyl-4-[1R,4-dimethyl-2R,3R-difluoro)pentanyloxy]-3-fluorobenzoate (MDW235)

The synthesis of 4'-decyloxyphenyl-4-[1R,4-dimethyl-2R,3R -difluoro)pentanyloxy]-3-fluorobenzoate, a diastereomer of 4'-decyloxyphenyl-4-[1S,4-dimethyl-2R,3R-difluoro)pentanyloxy]-3-fluorobenzoate (Example 5a), the method of Example 5a was followed with the exception that 1S,4-dimethyl-(2S,3S -epoxy)pentanol (XVII, R$_2$=isopropyl) was used in place of 1R,4-dimethyl-(2S,3S-epoxy)pentanol (XIX, R$_2$=isopropyl).

4'-decyloxyphenyl-(4-hydroxy-3-fluoro)benzoate (1.0 mmol), 1S,4-dimethyl-(2S,3S-epoxy)pentanol (XVII, where R$_2$=isopropyl) (1.0 mmol) and triphenylphosphine (1.5 mmol) were dissolved in 10 ml of dry THF. A solution of diisopropyl azodicarboxylate (3 mmol) in 1 ml of dry THF was added dropwise over a period of two hours. The reaction mixture was stirred for two hours with a magnetic stirring bar. The solvent was then taken off under vacuum and the residue was flash chromatographed using 5% (v/v) ethyl acetate in hexanes as eluent to afford the 4'-decyloxyphenyl-4-[(1R,4-dimethyl-2S,3S -epoxy)pentanyloxy]-3-fluorobenzoate product (MDW207) in 84% yield.

240 mg (0.52 mmol) of the 4'-decyloxyphenyl-4-[(1R,4-dimethyl-2S,3S-epoxy)pentanyloxy]-3-fluorobenzoate was dissolved in 10 ml of dry CH$_2$Cl$_2$ and cooled to 0° C. 0.5 ml of HF in pyridine was added to the cold solution and stirred for one hour with a stirring bar. Completion of the reaction was determined by TLC. It was then quenched with cold water and stirred further for 15 minutes. The solvent was rotary evaporated and the residue was flash chromatographed on a silica column using 10% (v/v) ethyl acetate in hexanes to obtain 82% of the fluorohydrin product.

In a flame dried argon filled flask the fluorohydrin product (208 mg) from the above reaction, was dissolved in 20 ml of dry CH$_2$Cl$_2$ and cooled to −70° C. 0.1 ml of dimethyl aminosulfurtrifluoride (DAST) was added to the reaction mixture and was allowed to stir for two hours at −70° C. The reaction mixture was stored in the refrigerator overnight. It was quenched with cold NaHCO$_3$ solution and stirred for 15 minutes. The product was extracted in CHCl$_2$ (two 50 ml portions). Organic layers were combined and washed repeatedly with NaHCO$_3$ solution and brine, dried with MgSO$_4$, filtered and rotary evaporated. The residue was flash chromatographed on a silica column using 5% ethyl acetate in hexanes to obtain 45% yield. The final product, 4'-decyloxyphenyl-4-[1R,4-dimethyl-2R,3R -difluoro)pentanyloxy]-3-fluorobenzoate was further purified by crystallization from hexanes.

This invention has been described and illustrated by reference to several preferred embodiments, but it is not intended to limit the invention by doing so. It is intended that the invention encompass all enantiomers and regioisomers of the general formula:

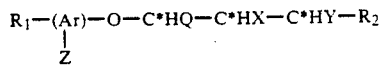

It is also intended that the invention include mixtures of two or more compositions of the subject invention, and FLC formulations in which these compounds are admixed with each other or with other compounds including LC and FLC materials.

What is claimed is:

1. A chiral nonracemic compound of the general formula:

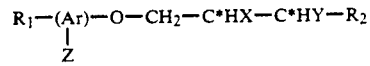

wherein:

R$_1$ is an achiral alkyl or alkenyl group of two to sixteen carbons,

Ar is either

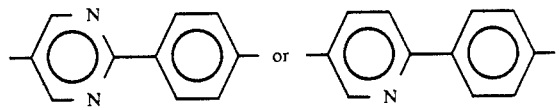

denotes a chiral carbon, R2 comprises the distal segment of the chiral tail and has one to ten carbon atoms, the —O—CH$_2$—C*HX—C—HY—R$_2$ segment comprises the chiral proximal segment of the chiral tail, and the proximal segment is selected from the diastereomers and enantiomers:

| | |
|---|---|
| 2S,3S-dihalo; | 2R,3R-dihalo; and |
| 2R,3S-dihalo; | 2S,3R-dhialo; | and Z represents one fluoride located ortho to the chiral proximal segment.

2. The compound of claim 1 wherein X and Y are both fluorine.

3. The compound of claim 1 wherein Ar is

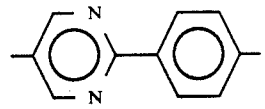

4. The compound of claim 3 wherein X and Y are both F.

5. The compound of claim 1 wherein R$_1$ is an alkyl group having two to sixteen carbon atoms.

6. The compound of claim 1 wherein the proximal segment is selected from the enantiomers 2S,3S-dihalo, and 2R,3R-dihalo.

7. The compound of claim 6 wherein X and Y are both fluorine.

8. An FLC composition comprising a compound of claim 1.

9. An FLC composition comprising a compound of claim 3.

10. An FLC composition comprising a compound of claim 4.

* * * * *

UNITED STATES PATENT AND TRADEMARK OFFICE
CERTIFICATE OF CORRECTION

PATENT NO. : 5,180,520

DATED : Jan. 19, 1993

INVENTOR(S) : Michael Wand; Rohini Vohra; David Walba

It is certified that error appears in the above-indentified patent and that said Letters Patent is hereby corrected as shown below:

Title page, item [54] and col. 1, lines 3-4, delete "HALOGENATED CORES AND CHIRAL".
Column 5, line 61, "phenylprdines." should read --phenylpyridines.--

Column 15, "Scheme 3" should read as follows:

--

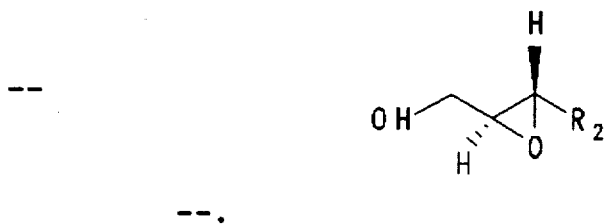

--.

In column 16, Scheme 3, please replace the formula for XII with:

--

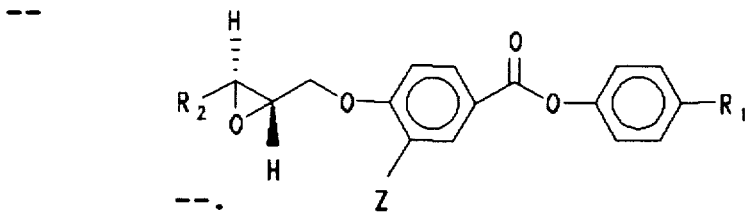

--.

In column 16, Scheme 5, please replace formula XVII with:

--

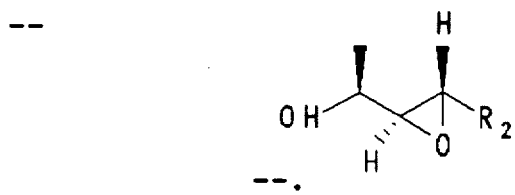

--.

UNITED STATES PATENT AND TRADEMARK OFFICE
CERTIFICATE OF CORRECTION

PATENT NO. : 5,180,520
DATED : Jan. 19, 1993
INVENTOR(S) : Michael Wand; Rohini Vohra; David Walba It is certified that error appears in the above-indentified patent and that said Letters Patent is hereby corrected as shown below:

In column 16, Scheme 5, please replace formula XVIII with:

--
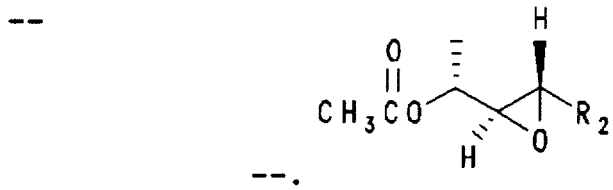
--.

In column 16, Scheme 5, in column 17, Scheme 6, and in column 17, scheme 7, all three occurrences, please replace formula XIX with:

--
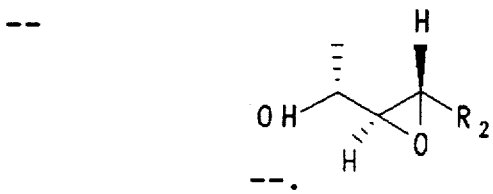
--.

In column 18, Scheme 6, please replace formula XX with:

--
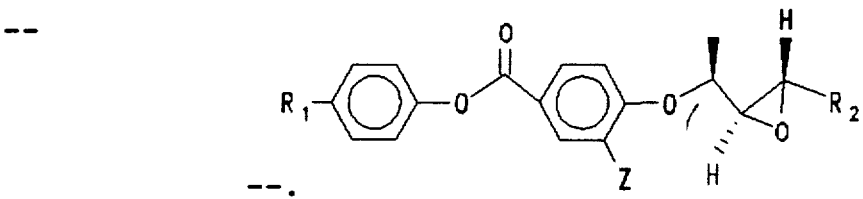
--.

UNITED STATES PATENT AND TRADEMARK OFFICE
CERTIFICATE OF CORRECTION

PATENT NO. : 5,180,520

DATED : Jan. 19, 1993

INVENTOR(S) : Michael Wand; Rohini Vohra; David Walba

It is certified that error appears in the above-indentified patent and that said Letters Patent is hereby corrected as shown below:

In column 18, Scheme 7, please replace formula XXIII with:

-- 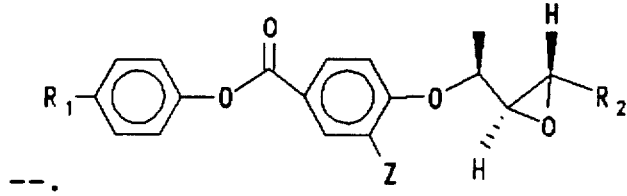 --.

At column 21, next-to-last line of Table 2, please rewrite "[1(R,4-dimethyl-" as --[(1(S,4-dimethyl- --. At column 21, last line of Table 2, "2R,3R-difluoro)pentyloxy]" should read --2R,3R-difluoropentyloxy]-3-fluorobenzoate--. At column 25, line 20, please rewrite "of4'-" as --of 4'- --.

Signed and Sealed this

Twenty-second Day of March, 1994

Attest:

BRUCE LEHMAN

Attesting Officer  Commissioner of Patents and Trademarks